US009445894B2

(12) United States Patent
Heldman

(10) Patent No.: US 9,445,894 B2
(45) Date of Patent: Sep. 20, 2016

(54) PROSTHETIC HEART VALVE WITH LINKING ELEMENT AND METHODS FOR IMPLANTING SAME

(71) Applicant: Alan W. Heldman, Miami, FL (US)

(72) Inventor: Alan W. Heldman, Miami, FL (US)

(*) Notice: Subject to any disclaimer, the term of this patent is extended or adjusted under 35 U.S.C. 154(b) by 0 days.

(21) Appl. No.: 14/307,009

(22) Filed: Jun. 17, 2014

(65) Prior Publication Data
US 2015/0073542 A1    Mar. 12, 2015

Related U.S. Application Data

(60) Provisional application No. 61/835,710, filed on Jun. 17, 2013.

(51) Int. Cl.
*A61F 2/24* (2006.01)
*A61B 5/026* (2006.01)

(52) U.S. Cl.
CPC .......... *A61F 2/2418* (2013.01); *A61F 2/2412* (2013.01); *A61B 5/026* (2013.01); *A61F 2210/009* (2013.01); *A61F 2220/0025* (2013.01); *A61F 2220/0091* (2013.01)

(58) Field of Classification Search
CPC ............................... A61F 2/24; A61F 2/2418
USPC ................................. 623/2.1–2.19
See application file for complete search history.

(56) References Cited

U.S. PATENT DOCUMENTS

| 7,955,377 | B2* | 6/2011 | Melsheimer | A61F 2/2418 623/1.24 |
| 8,226,707 | B2* | 7/2012 | White | A61F 2/2412 623/1.12 |
| 8,685,080 | B2* | 4/2014 | White | A61F 2/2412 623/1.26 |
| 2001/0007956 | A1 | 7/2001 | Letac et al. | |
| 2006/0271171 | A1 | 11/2006 | McQuinn et al. | |
| 2007/0168024 | A1* | 7/2007 | Khairkhahan | A61F 2/2403 623/2.18 |
| 2008/0275540 | A1 | 11/2008 | Wen | |
| 2010/0036485 | A1 | 2/2010 | Seguin | |
| 2010/0217382 | A1 | 8/2010 | Chau et al. | |
| 2010/0249923 | A1* | 9/2010 | Alkhatib | A61F 2/2418 623/2.18 |
| 2011/0213461 | A1* | 9/2011 | Seguin | A61F 2/2418 623/2.18 |
| 2011/0319989 | A1* | 12/2011 | Lane | A61F 2/2418 623/2.11 |
| 2012/0053682 | A1* | 3/2012 | Kovalsky | A61F 2/2418 623/2.11 |
| 2012/0078347 | A1* | 3/2012 | Braido | A61F 2/2418 623/1.26 |
| 2012/0172982 | A1* | 7/2012 | Stacchino | A61F 2/2418 623/2.17 |

* cited by examiner

*Primary Examiner* — Suzette J Gherbi
(74) *Attorney, Agent, or Firm* — Lott & Fischer, PL

(57) ABSTRACT

Disclosed is a prosthetic heart valve incorporating one or more linking elements adapted for anchoring, aligning, stabilizing, fixing, or otherwise enabling the implantation of other prosthetic devices, including other prosthetic heart valves, in or around the heart.

38 Claims, No Drawings

PROSTHETIC HEART VALVE WITH LINKING ELEMENT AND METHODS FOR IMPLANTING SAME

CLAIM OF PRIORITY

This application is being filed as a non-provisional patent application under 35 U.S.C. §111(b) and 37 CFR §1.53(c). This application claims priority under 35 U.S.C. §111(e) to U.S. provisional patent application Ser. No. 61/835,710 filed on Jun. 17, 2013, the contents of which are incorporated herein by reference.

TECHNICAL FIELD

This invention relates generally to prosthetic heart valves and in particular to prosthetic heart valves incorporating one or more linking elements adapted for anchoring, aligning, stabilizing, fixing, or otherwise enabling the implantation of other prosthetic devices, including other prosthetic heart valves, in or around the heart.

BACKGROUND OF THE INVENTION

The function of the four valves in the mammalian heart (including that of humans) is to enable forward propulsion of blood without regurgitation, or backwards flow. The valves sit in between the chambers of the heart and its great vessels. The left heart pumps oxygenated blood under high pressure to the systemic circulation, while the right heart pumps deoxygenated blood under lower pressure to the pulmonary circulation.

The left and right heart each have two valves: the atrioventricular valves, and the semilunar valves. In the left heart, these are the mitral and aortic valves, respectively. In the right heart, these are the tricuspid and pulmonic valves. The atrioventricular valves divide the atria (low pressure filling chambers) from the ventricles (muscular pumping chambers). The semilunar valves separate the ventricles from their outflow great vessels.

Focusing for now on the cardiac cycle of the left side of the heart, the normally functioning mitral (atrioventricular) valve opens to permit the left atrium to empty under low pressure into the relaxed left ventricle during diastole. At the onset of ventricular systole, rising pressure in the left ventricle closes the mitral valve, so that blood does not flow back into the left atrium. When left ventricular pressure rises to exceed that in the aorta, the aortic (semilunar) valve opens to permit left ventricular ejection of blood into the aorta. When the left ventricle has completed its ejection phase, and begins to relax, the aortic valve falls closed, preventing blood from regurgitating into the left ventricle. During isovolumic relaxation, the ventricular pressure falls with both aortic and mitral valves closed. Then the mitral valve opens allowing left atrial emptying again into the low pressure left ventricle, and pressure-volume cycling begins again. A similar sequence takes place in the right heart with its tricuspid and pulmonic valves, right atrium and ventricle, and pulmonary artery.

The cardiac valves in humans may be affected by a variety of congenital and acquired disorders. The functional result of these disorders may include:

1. Valvular stenosis, whereby a failure of the valve to open completely causes increased resistance to blood flow across that valve.

2. Valvular regurgitation, whereby failure of the valve (or associated structures) to close completely permits blood to leak backwards into the normally protected chamber.

The consequences of valvular stenosis and regurgitation produce major human disease, including congestive heart failure, adverse remodeling of the cardiac chambers, disabling symptoms, heart rhythm disturbances, decreased functional capacity, and death. For these reasons, medical science includes treatments to repair, to replace, or to supplement abnormally functioning heart valves.

One strategy to treat malfunctioning heart valves is to implant into the heart a prosthetic valve which supplements or replaces the functions of the diseased valve. For example, the transcatheter implantation of a prosthetic valve into the position of the aortic, or the pulmonic valve (the semilunar valves) has been used successfully to treat both stenosis and regurgitation of these valves. In many such applications, the transcatheter valve is implanted without removing the diseased or malfunctioning semilunar valve; in this way the malfunctioning valve's tissue is excluded from the main path of blood flow, and its function is partially or wholly replaced by the new valve. In addition to the treatment of diseased native valves, prosthetic or transplanted heart valves can also be treated in this fashion.

The structure and function of the semilunar valves differ importantly from those of the atrioventricular valves. Features which are significant for purposes of the present disclosure include:

1. The circular or mildly elliptical conformation of tissue, with low distensibility, surrounding the semilunar valves.

2. The tubular nature of the ventricular outflow tract (below the semilunar valves) and of the great vessels (above the semilunar valves).

3. The higher velocity and pressurized nature of flow across the semilunar valves compared to the atrioventricular valves.

4. The complex three-dimensional structure of the atrioventricular valves.

For these and other reasons, there is a need in the art for methods and devices that utilize certain aspects of the semilunar valve complex and its surrounding tissues for the purposes of anchoring, aligning, stabilizing, fixing, or otherwise enabling the implantation of prosthetic devices into the atrioventricular valve and elsewhere in the heart or in the vicinity thereof.

DETAILED DESCRIPTION OF THE INVENTION

While the present invention will be described more fully hereinafter, it is to be understood at the outset of the description which follows that persons of skill in the appropriate arts may modify the invention herein described while still achieving the favorable results of this invention. Accordingly, the description which follows is to be understood as being a broad, teaching disclosure directed to persons of skill in the appropriate arts, and not as limiting upon the present invention.

The herein disclosed invention describes, among other embodiments, a prosthetic heart valve, for example in the semilunar valve position, incorporating one or more linking elements adapted for anchoring, aligning, stabilizing, fixing, or otherwise enabling the implantation of other prosthetic devices, including other prosthetic heart valves, in or around the heart.

There are many examples of prosthetic heart valves known in the prior art, all of which are suitable for adaptation to the linking elements described in the present disclosure. Among those devices are, for example, the prosthetic semilunar heart valves described in U.S. Pat. Nos. 7,585,321, 7,846,203, 7,846,204, 6,908,481, 8,002,825, 8,057,540, 8,579,966, 8,591,575, and 8,721,708 as well as U.S. Patent Application Publication Nos. 201100036485 20140163672, and 20140005774, all of which are incorporated by reference in the present disclosure.

In one embodiment, the invention encompasses the use of a linking element between a prosthetic device in the position of the semilunar valve, and a prosthetic device in the position of the atrioventricular valve.

In one such embodiment, a transcatheter-implanted aortic valve is physically connected by one or more mechanical linking elements to an implanted mitral valve. The one or more linking elements provide an anchor and additional stability to the implanted mitral valve and additionally may provide for better alignment of the implanted mitral valve relative to the annulus of the native mitral valve and to the other structures of the native mitral valve apparatus.

In another such embodiment, a transcatheter-implanted pulmonic valve is physically connected by one or more mechanical linking elements to an implanted tricuspid valve, providing similar stability and alignment benefits.

In some embodiments of the present invention, the described fixation elements may supplement other alignment or fixation components to improve the positioning, and/or stability of an implanted device.

In another embodiment of the present invention, components other than an implanted heart valve are connected to an implanted semilunar valve by one or more mechanical linking elements. These components may be connected to the implanted semilunar valve in addition to, or instead of, a second implanted heart valve.

The additional components may include devices that perform functions within the heart other than to control blood flow between the various chambers of the heart and/or blood vessels. For example, such components may include devices involved in electrically stimulating the heart (such as pacemakers and implanted defibrillators). Such components may also include components of a cardiac assist pump and/or devices which permit monitoring of heart function, of intracardiac pressure, of blood flow, or of electrical activity within the heart. Such components may also include devices which maintain or assist blood flow within the coronary arteries of the heart, such as stents.

The one or more linking elements of the present invention are formed of biocompatible materials that are well known in the relevant art. Such materials can be metallic (stainless steel, silver, gold, titanium, cobalt chromium and other biocompatible metals), plastic polymers, ceramics, or other known biocompatible materials. Said linking elements can have varying degrees of rigidity depending on the application.

The one or more linking elements of the present invention can be formed as a single piece or may be formed from sub components that can be connected so as to permit articulation within the link.

The one or more linking elements of the present invention may be comprised of a suture, fiber, cable, or other similar material permitting tightening, tensioning, adjusting, and tying of the linkage as needed.

The one or more linking elements of the present invention can be integrally formed into the implanted semilunar valve or may be removably attached to the implanted semilunar valve. The connection between the semilunar valve and one or more linking elements may be rigid, flexible or articulated (through, for example, a hinged joint, a snap-together joint, a ball-and-socket joint, or similar mechanism) depending on the required application.

Similarly, the connection between the one or more linking elements, and the component or components to be anchored or supported by the implanted semilunar valve may be rigid, flexible or articulated depending on the required application.

In another embodiment of the present invention, the linking element utilizes magnetic forces to connect to the implanted semilunar valve or the device to be anchored thereto. A magnetic connection between the linking element and the implanted semilunar valve or other device may significantly assist in orienting the device and valve relative to each other.

In a variation of this embodiment, the magnetic force may be exerted across a distance so that the linked components are not necessarily in direct physical contact with one another.

The advantages for medical science, practitioners, and patients of the disclosed invention include but are not limited to:

1. Stabilization of an atrioventricular valve prosthesis in its position.
2. Orientation of an atrioventricular prosthesis in the desired position.
3. Reduction of the forces of annular expansion and distortion imposed on the heart by an atrioventricular valve prosthesis.
4. Accurate positioning of diagnostic or therapeutic elements within the heart.

An embodiment of the present invention can be used through the following method. First an aortic valve prosthesis is implanted into its physiologic position, using any of several techniques, including but not limited to:

transcatheter retrograde delivery
transcatheter anterograde delivery
surgical implantation The aortic valve prosthesis is assembled (either prior to implantation, or subsequent to implantation in the body) with one or more of the linking elements described, in an attachment to the main structure of the device.

To utilize the aortic valve prosthesis with linking element, the operator connects the secondarily implanted device (for example, a mitral valve prosthesis) to the linking element. This connection may be accomplished by transcatheter capture or the linking element from any of several access approaches, including but not limited to transcatheter (via access retrograde across the aortic valve, transseptal antegrade across the mitral valve, or from the left ventricle transapical) or any surgical approach to the heart.

Once the connection between the primary valve and the secondary device has been made, the operator completes the implantation of the secondary device, utilizing the linking element for its intended purposes of stabilization, orientation, or fixation of the secondary device.

It will be understood by those having ordinary skill in the art that although in the above description an implanted semilunar valve prosthesis is the base to which an implanted atrioventricular valve prosthesis, or other device is anchored to, a reciprocal arrangement is also comprehended by the present invention. That is, an implanted atrioventricular valve prosthesis may serve as the base to which an implanted semilunar valve prosthesis, or other device, is anchored.

Accordingly, it will be understood that several embodiments of the present invention have been disclosed by way of example and that other modifications and alterations may occur to those skilled in the art without departing from the scope and spirit of the appended claims.

What is claimed is:

1. A prosthetic heart valve assembly comprising:
   an implantable prosthetic cardiac valve configured to permit blood flow in a first direction and to inhibit blood flow in a second direction opposite the first direction;
   a radially collapsible and expandable annular support frame supporting said prosthetic cardiac valve;
   one or more linking elements connected to said support frame, each having a terminal end extending distally from said support frame;
   wherein each of said terminal ends is adapted to connect to a heart implantable device; and
   wherein the connection between the support frame and at least one of said linking elements is magnetic.

2. The prosthetic heart valve assembly of claim 1, wherein said implantable prosthetic cardiac valve is a valve prosthesis selected from the group consisting of an aortic valve prosthesis, a pulmonic valve prosthesis, a mitral valve prosthesis and a tricuspid valve prosthesis.

3. The prosthetic heart valve assembly of claim 1, wherein said heart implantable device is a device selected from the group consisting of an aortic valve prosthesis, a pulmonic valve prosthesis, a mitral valve prosthesis, a tricuspid valve prosthesis, and components thereof.

4. The prosthetic heart valve assembly of claim 1, wherein said heart implantable device is a device selected from the group consisting of an aortic valve prosthesis, a pulmonic valve prosthesis, a mitral valve prosthesis, a tricuspid valve prosthesis, a pacemaker, a defibrillator, a cardiac assist pump, a blood flow monitor, an electrical activity monitor, a stein, and components thereof.

5. The prosthetic heart valve assembly of claim 1 wherein at least one of said one or more linking elements is formed at least partially of a biocompatible material selected from the group consisting of stainless steel, silver, gold, titanium, cobalt chromium, plastic polymer, pyrolytic carbon, suture, fiber, filament, cable and combinations thereof.

6. The prosthetic heart valve assembly of claim 1 wherein at least one of said one or more linking elements comprises a single component.

7. The prosthetic heart valve assembly of claim 1 wherein at least one of said one or more linking elements comprises a plurality of subcomponents in an articulated arrangement.

8. The prosthetic heart valve assembly of claim 1 wherein at least one of said one or more linking elements is rigid.

9. The prosthetic heart valve assembly of claim 1 wherein at least one of said one or more linking elements is flexible.

10. The prosthetic heart valve assembly of claim 1 wherein the connection between said support frame and at least one of said one or more linking elements is rigid.

11. The prosthetic heart valve assembly of claim 1 wherein the connection between said support frame and at least one of said one or more linking elements is articulated.

12. The prosthetic heart valve assembly of claim wherein the connection between said support frame and at least one of said one or more linking elements is flexible.

13. The prosthetic heart valve assembly of claim 1 wherein at least one of said terminal ends is adapted to connect to said heart implantable device using an articulated joint.

14. The prosthetic heart valve assembly of claim 1 wherein at least one of said terminal ends is adapted to connect to said heart implantable device using a magnetic joint.

15. The prosthetic heart valve assembly of claim 1 wherein at least one of said one or more linking elements is adjustable by tightening, loosening, rotating or redirecting.

16. A linking element connecting heart implantable devices comprising:
    an elongated component having a first terminal end and a second terminal end;
    wherein said first terminal end is adapted to connect to a first heart implantable device;
    wherein said second terminal end is adapted to connect to a second heart implantable device; and
    wherein at least one of said first terminal end or said second terminal end are adapted to connect to one of said first heart implantable device or second heart implantable device using a magnetic joint.

17. The linking element of claim 16 wherein at least one of said first heart implantable device and said second heart implantable device are selected from the group consisting of an aortic valve prosthesis, a pulmonic valve prosthesis, a mitral valve prosthesis, a tricuspid valve prosthesis, a pacemaker, a defibrillator, a cardiac assist pump, a blood flow monitor, an electrical activity monitor, a stent, and components thereof.

18. The linking element of claim 16 wherein said linking elements is formed at least partially of a biocompatible material selected from the group consisting of stainless steel, silver, gold, titanium, cobalt chromium, plastic polymer, pyrolytic carbon, suture, fiber, filament, cable and combinations thereof.

19. The linking element of claim 16 wherein said linking element comprises a plurality of subcomponents in an articulated arrangement.

20. The linking element of claim 16 wherein said linking element is rigid.

21. The linking element of claim 16 wherein said linking element is flexible.

22. The linking element of claim 16 wherein said linking element is adjustable by tightening, loosening, rotating or redirecting.

23. The linking element of claim 16 wherein at least one of said first terminal end said second terminal end are adapted to connect to one of said first heart implantable device or second heart implantable device using an articulated joint.

24. A prosthetic heart valve assembly comprising:
    at implantable prosthetic cardiac valve configured to permit blood flow in a first direction and to inhibit blood flow in a second direction opposite the first direction;
    a radially collapsible and expandable annular support frame supporting said prosthetic cardiac valve;
    one or more linking elements connected to said support frame, each having, a terminal end extending distally from said support frame;
    wherein each of said terminal ends is adapted to connect to a heart implantable device; and
    wherein at least one of said terminal ends is adapted to connect to said heart implantable device using a magnetic joint.

25. The prosthetic heart valve assembly of claim 24, wherein said implantable prosthetic cardiac valve is a valve prosthesis selected from the group consisting of an aortic valve prosthesis, a pulmonic valve prosthesis, a mitral valve prosthesis and a tricuspid valve prosthesis.

26. The prosthetic heart valve assembly of claim 24, wherein said heart implantable device is a device selected from the group consisting of an aortic valve prosthesis, a pulmonic valve prosthesis, a mitral valve prosthesis, a tricuspid valve prosthesis, and components thereof.

27. The prosthetic heart valve assembly of claim 24, wherein said heart implantable device is a device selected from the group consisting of an aortic valve prosthesis, a pulmonic valve prosthesis, a mitral valve prosthesis, a tricuspid valve prosthesis, a pacemaker, a defibrillator, a cardiac assist pump, a blood flow monitor, an electrical activity monitor, a stem, and components thereof.

28. The prosthetic heart valve assembly of claim 24, wherein at least one of said one or more linking elements is formed at least partially of a biocompatible material selected from the group consisting of stainless steel, silver, gold, titanium, cobalt chromium, plastic polymer, pyrolytic carbon, suture, fiber, filament, cable and combinations thereof.

29. The prosthetic heart valve assembly of claim 24, wherein at least one of said one or more linking elements comprises a single component.

30. The prosthetic heart valve assembly of claim 24, wherein at least one of said one or more linking elements comprises a plurality of subcomponents in an articulated arrangement.

31. The prosthetic heart valve assembly of claim 24, wherein at least one of said one or more linking elements is rigid.

32. The prosthetic heart valve assembly of claim 24, wherein at least one of said one or more linking elements is flexible.

33. The prosthetic heart valve assembly of claim 24, wherein the connection between said support frame and at least one of said one or more linking elements is rigid.

34. The prosthetic heart valve assembly of claim 24, wherein the connection between said support frame and at least one of said one or more linking elements is articulated.

35. The prosthetic heart valve assembly of claim 24, wherein the connection between said support frame and at least one of said one or more linking elements is flexible.

36. The prosthetic heart valve assembly of claim 24, wherein the connection between said support frame and at least one of said one or more linking elements is magnetic.

37. The prosthetic heart valve assembly of claim 24, wherein at least one of said terminal ends is adapted to connect to said heart implantable device using an articulated joint.

38. The prosthetic heart valve assembly of claim 24, wherein at least one of said one or more linking elements is adjustable by tightening, loosening, rotating or redirecting.

* * * * *